United States Patent
Small

(10) Patent No.: US 11,878,952 B1
(45) Date of Patent: Jan. 23, 2024

(54) OLIGOMERIZATION CATALYST SYSTEM DEACTIVATION AND RELATED ETHYLENE OLIGOMERIZATION PROCESSES

(71) Applicant: Chevron Phillips Chemical Company LP, The Woodlands, TX (US)

(72) Inventor: Brooke L. Small, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 18/054,934

(22) Filed: Nov. 14, 2022

(51) Int. Cl.
*C07C 2/08* (2006.01)

(52) U.S. Cl.
CPC ............ *C07C 2/08* (2013.01); *C07C 2521/02* (2013.01); *C07C 2531/22* (2013.01)

(58) Field of Classification Search
None
See application file for complete search history.

(56) References Cited

U.S. PATENT DOCUMENTS

| | | | |
|---|---|---|---|
| 3,662,021 A | 5/1972 | Langer, Jr. | |
| 4,409,414 A | 10/1983 | Langer, Jr. | |
| 4,486,615 A | 12/1984 | Langer, Jr. | |
| 4,701,504 A | 10/1987 | Mitchell | |
| 5,563,312 A | 10/1996 | Knudsen | |
| 5,689,028 A | 11/1997 | Lashier | |
| 5,731,381 A | 3/1998 | Apecetche | |
| 5,750,816 A | 5/1998 | Araki | |
| 5,856,612 A | 1/1999 | Araki | |
| 5,910,619 A | 6/1999 | Urata | |
| 6,133,495 A | 10/2000 | Urata | |
| 7,157,612 B2 | 1/2007 | Ewert | |
| 8,049,052 B2 * | 11/2011 | Kreischer | B01J 31/122 585/512 |
| 8,957,235 B2 | 2/2015 | Sydora | |
| 9,175,109 B1 | 11/2015 | Kreischer | |
| 9,382,348 B2 | 7/2016 | Kufeld | |
| 9,505,675 B2 | 11/2016 | Sydora | |
| 9,580,453 B2 | 2/2017 | Sydora | |
| 9,617,358 B2 | 4/2017 | Kufeld | |
| 9,732,300 B2 | 8/2017 | Kilgore | |
| 9,956,548 B2 | 5/2018 | Sydora | |

(Continued)

FOREIGN PATENT DOCUMENTS

WO 2013095720 A1 6/2013
WO 2015179337 A1 11/2015

(Continued)

*Primary Examiner* — Ali Z Fadhel
(74) *Attorney, Agent, or Firm* — Merchant & Gould P.C.

(57) ABSTRACT

Methods for deactivating a transition metal-based catalyst system containing a co-catalyst comprising an aluminoxane and optionally an alkylaluminum are disclosed in which the catalyst system is contacted with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}. Related methods for deactivating a residual catalyst system in reactor effluent streams and related ethylene oligomerization processes also are described.

24 Claims, 1 Drawing Sheet

(56) References Cited

U.S. PATENT DOCUMENTS

| | | | |
|---|---|---|---|
| 10,435,336 B2 | 10/2019 | Kreischer | |
| 10,464,862 B2 | 11/2019 | Bischof | |
| 10,493,422 B2 | 12/2019 | Bischof | |
| 10,513,473 B2 | 12/2019 | Kreischer | |
| 10,519,077 B2 | 12/2019 | Kreischer | |
| 10,550,252 B2 | 2/2020 | Beaulieu | |
| 10,577,440 B2 | 3/2020 | Cruz | |
| 10,632,446 B2 | 4/2020 | Uhm | |
| 10,654,948 B2 | 5/2020 | Cruz | |
| 10,927,054 B2 | 2/2021 | Kreischer | |
| 11,027,255 B2 | 6/2021 | Uhm | |
| 11,186,707 B2 | 11/2021 | Beaulieu | |
| 11,267,909 B2 | 3/2022 | Bischof | |
| 2007/0161839 A1 | 7/2007 | Woodard | |
| 2015/0291486 A1* | 10/2015 | Weber | C08F 2/42 |
| | | | 585/512 |
| 2016/0325263 A1 | 11/2016 | Uhm | |
| 2018/0258009 A1* | 9/2018 | Alqahtani | C07C 2/22 |

FOREIGN PATENT DOCUMENTS

| | | |
|---|---|---|
| WO | 2016130400 A1 | 8/2016 |
| WO | 2017010998 A1 | 1/2017 |
| WO | 2017011127 A1 | 1/2017 |
| WO | 2022132745 A1 | 6/2022 |

* cited by examiner

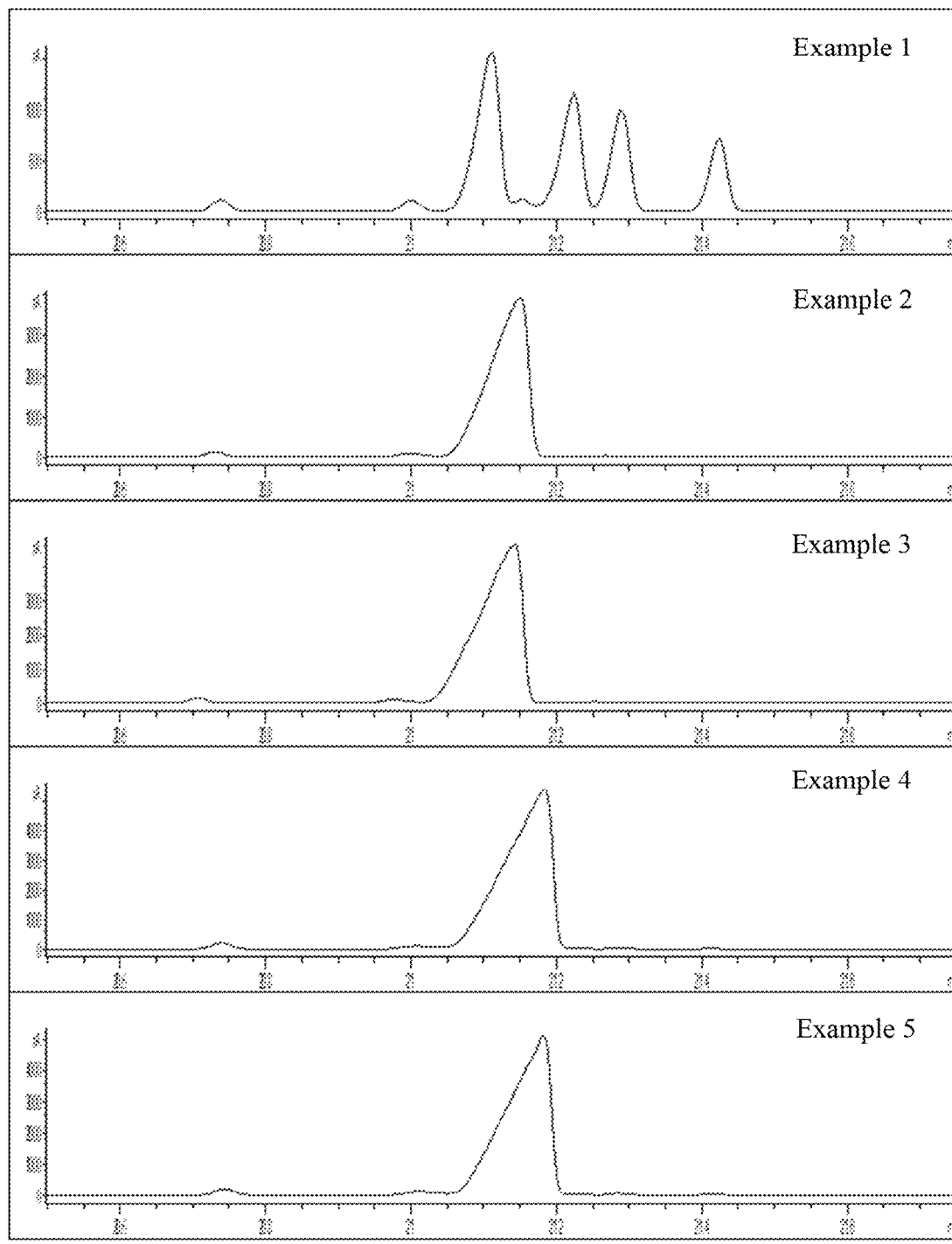

US 11,878,952 B1

OLIGOMERIZATION CATALYST SYSTEM DEACTIVATION AND RELATED ETHYLENE OLIGOMERIZATION PROCESSES

FIELD OF THE INVENTION

The present disclosure relates generally to methods for deactivating catalyst systems, and more particularly, relates to deactivating catalyst systems containing aluminoxane and alkylaluminum co-catalysts.

BACKGROUND OF THE INVENTION

There are various multicomponent catalyst systems that are suitable for oligomerizing ethylene to produce 1-hexene or 1-octene. Once the oligomer product has been formed in an oligomerization reactor and thereafter discharged, it is often desirable to deactivate the catalyst system to prevent further oligomerization of ethylene, as well as to prevent isomerization of the 1-hexene or 1-octene product. It is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Methods for deactivating catalyst systems are described herein. In one aspect, for instance, a method for deactivating a transition metal-based catalyst system containing a co-catalyst comprising an aluminoxane and optionally an alkylaluminum can comprise contacting the catalyst system with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

Another method is directed to deactivating a residual transition metal-based catalyst system containing a co-catalyst comprising an aluminoxane and optionally an alkylaluminum in an effluent stream from an oligomerization reactor. This method can comprise contacting the effluent stream— the effluent stream comprising unreacted ethylene, an oligomer product, the residual transition metal-based catalyst system containing the co-catalyst comprising the aluminoxane and optionally the alkylaluminum, and an organic reaction medium—with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

Also described herein are oligomerization processes. A representative process can comprise A) introducing ethylene, a transition metal-based catalyst system or catalyst system components, an organic reaction medium, and optionally hydrogen, into an oligomerization reactor, the transition metal-based catalyst system or catalyst system components containing a co-catalyst comprising an aluminoxane and optionally an alkylaluminum, B) forming an oligomer product in the oligomerization reactor, the oligomer product comprising hexenes and octenes, C) discharging an effluent stream from the oligomerization reactor, the effluent stream comprising unreacted ethylene, the oligomer product, a residual transition metal-based catalyst system containing the co-catalyst comprising the aluminoxane and optionally the alkylaluminum, and the organic reaction medium, and D) contacting the effluent stream with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE FIGURE

FIG. 1 presents gas chromatograph plots of the oligomerization experiments of Examples 1-5.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise. The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon).

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has a carbon-carbon double bond between the first and second carbon atom of the longest contiguous chain of carbon atoms. The term "alpha olefin" includes linear and branched alpha olefins and alpha olefins which can have more than one non-aromatic carbon-carbon double bond, unless expressly stated otherwise. The term "normal alpha olefin" as used herein refers to a linear aliphatic hydrocarbon mono-olefin having a carbon-carbon double bond between the first and second carbon atoms. The term "linear internal olefin" as used herein refers to a linear aliphatic hydrocarbon mono-olefin having a double bond that is not between the first and second carbon atom.

The term "oligomer" refers to a compound that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer), but exclude other non-oligomer components of an oligomerization reactor effluent stream, such as unreacted ethylene, organic reaction medium, and hydrogen, amongst other components.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the aluminoxane and/or alkylaluminum and the transition metal compound or complex after combining these components. Therefore, the terms "catalyst composition," "catalyst mixture," "catalyst system," and the like, encompass the initial starting components of the composition, as well as whatever product(s) may result from contacting these initial starting components. The terms "catalyst composition," "catalyst mixture," "catalyst system," and the like, may be used interchangeably throughout this disclosure.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a co-catalyst deactivating agent is a $C_4$ to $C_{18}$ alcohol, or in alternative language, an alcohol having from 4 to 18 carbon atoms, as used herein, refers to an alcohol compound that can have 4, 5, 6, 7, 8, 9, 10, 11, 12, 13, 14, 15, 16, 17, or 18 carbon atoms, as well as any range between these two numbers (for example, a $C_6$-$C_{16}$ alcohol or a $C_8$-$C_{12}$ alcohol), and also including any combination of ranges between these two numbers (for example, a $C_6$ to $C_{10}$ and a $C_{14}$ to $C_{18}$ alcohol). Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods and materials similar or equivalent to those described herein can be used in the practice or testing of the invention, the typical methods and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

Catalyst systems for the oligomerization of ethylene are deactivated herein with a co-catalyst deactivating agent at surprisingly low amounts of OH of the co-catalyst deactivating agent, based on the amount of aluminum in the aluminoxane and alkylaluminum co-catalysts present in the catalyst system.

Deactivation Methods

In one aspect, a method for deactivating a residual transition metal-based catalyst system containing a co-catalyst comprising an aluminoxane, and optionally an aluminoxane is disclosed herein. This method can comprise contacting the catalyst system with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

In another aspect, a method for deactivating a residual transition metal-based catalyst system containing a co-catalyst comprising an aluminoxane and optionally an alkylaluminum in an effluent stream from an oligomerization reactor is disclosed herein. This method can comprise contacting the effluent stream (the effluent stream comprising unreacted ethylene, an oligomer product, the residual transition metal-based catalyst system containing the co-catalyst comprising the aluminoxane and optionally the alkylaluminum, and an organic reaction medium) with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

In yet another aspect, an oligomerization process is disclosed herein. This process can comprise A) introducing ethylene, a transition metal-based catalyst system or catalyst system components, an organic reaction medium, and optionally hydrogen, into an oligomerization reactor, the transition metal-based catalyst system or catalyst system components containing a co-catalyst comprising an aluminoxane and optionally an alkylaluminum, B) forming an oligomer product in the oligomerization reactor, the oligomer product comprising hexenes and octenes, C) discharging an effluent stream from the oligomerization reactor, the effluent stream comprising unreacted ethylene, the oligomer product, a residual transition metal-based catalyst system containing the co-catalyst comprising the aluminoxane and optionally the alkylaluminum, and the organic reaction medium, and D) contacting the effluent stream with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

Generally, the features of the these methods/processes in which the catalyst system is deactivated (e.g., the co-catalyst, the relative amount of aluminoxane:alkylaluminum if both are present, the co-catalyst deactivating agent, and the relative amount of the co-catalyst deactivating agent, among others) are independently described herein and these features can be combined without limitation, and in any combination to further describe the disclosed methods/processes. Moreover, additional steps can be performed before, during, and/or after the steps of these methods/processes, and can be utilized without limitation and in any combination to further describe the methods for deactivating a catalyst system and the processes for oligomerizing ethylene, unless stated otherwise. Further, and beneficially, these methods/processes can be performed continuously.

In the disclosed methods/processes, the catalyst system can contain a co-catalyst comprising an aluminoxane and optionally an alkylaluminum. Thus, in some aspects, the co-catalyst comprises both the aluminoxane and the alkylaluminum, while in other aspects, the co-catalyst comprises the aluminoxane (and no alkylaluminum is present). When both the aluminoxane and the alkylaluminum are present in the catalyst system, the relative amounts of aluminoxane to alkylaluminum (aluminoxane:alkylaluminum) in the catalyst system are not particularly limited. Nonetheless, illustrative and non-limiting ranges include molar ratios of aluminoxane:alkylaluminum (based on aluminum) from 100:1 to 1:100, from 20:1 to 1:20, from 10:1 to 1:10, from 5:1 to 1:5, from 10:1 to 1:1, or from 8:1 to 2:1, and the like.

Often, the molar amount of aluminoxane in the catalyst system is greater than that of the alkylaluminum, but this is not a requirement.

Any suitable aluminoxane can be utilized in the catalyst system, such as methylaluminoxane (MAO), modified methylaluminoxane (MMAO), ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, as well as any mixture or combination thereof. In an aspect, the aluminoxane can comprise (or consist essentially of, or consist of) methylaluminoxane (MAO); alternatively, modified methylaluminoxane (MMAO); alternatively, ethylaluminoxane; alternatively, n-propylaluminoxane; alternatively, iso-propylaluminoxane; alternatively, n-butylaluminoxane; alternatively, t-butylaluminoxane; alternatively, sec-butylaluminoxane; alternatively, iso-butylaluminoxane; alternatively, 1-pentylaluminoxane; alternatively, 2-pentylaluminoxane; alternatively, 3-pentylaluminoxane; alternatively, isopentylaluminoxane; or alternatively, neopentylaluminoxane.

Likewise, the alkylaluminum utilized in the catalyst system is not particularly limited, and representative alkylaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, and the like, as well as any mixture or combination thereof. In an aspect, the alkylaluminum can comprise (or consist essentially of, or consist of) trimethylaluminum (TMA); alternatively, triethylaluminum (TEA); alternatively, tri-n-propylaluminum (TNPA); alternatively, tri-n-butylaluminum (TNBA); alternatively, triisobutylaluminum (TIBA); alternatively, tri-n-hexylaluminum; or alternatively, tri-n-octylaluminum.

The molar amount of OH of the co-catalyst deactivating agent in the disclosed methods/processes falls within a range from 0.5 to 1.5 times {(moles of aluminum of the aluminoxane)+(moles aluminum of the alkylaluminum)+(moles aluminum of the alkylaluminum)}. The number ranging from 0.5 to 1.5 also can be referred to as the effective amount of quench OH needed based on aluminum. In an aspect, the minimum molar amount of OH (or minimum effective amount of quench OH) can be at least 0.5, 0.6, 0.7, 0.8, 0.9, 1, or 1.1, and in another aspect, the maximum molar amount of OH (or maximum effective amount of quench OH) can be 1.5, 1.4, 1.3, or 1.2. Generally, the molar amount of OH to the moles of aluminum (or the effective amount of quench OH based on aluminum) can range from any minimum amount to any maximum amount described herein. For instance, the molar amount of OH of the co-catalyst deactivating agent can be from 0.5 to 1.4 times, from to 1.3 times, from 0.6 to 1.5 times, from 0.6 to 1.4 times, from 0.6 to 1.3 times, from 0.6 to 1.2 times, from 0.7 to 1.5 times, from 0.7 to 1.4 times, from 0.7 to 1.3 times, from 0.7 to 1.2 times, from 0.8 to 1.4 times, from 0.8 to 1.3 times, from 0.9 to 1.5 times, from 0.9 to 1.4 times, from 0.9 to 1.3 times, from 1 to 1.5 times, from 1 to 1.4 times, from 1 to 1.3 times, from 1.1 to 1.5 times, from 1.1 to 1.4 times, or from 1.1 to 1.3 times {(moles of aluminum of the aluminoxane)+(moles aluminum of the alkylaluminum)+(moles aluminum of the alkylaluminum)}. While not wishing to be bound by the following theory, it is believed that molar amounts of OH in excess of 1.5 result in more free alcohol in the oligomerization system that might be recycled and negatively impact the fresh catalyst entering the reactor, as well as leading to material waste and cost inefficiency. Conversely, it is believed that molar amounts less than 0.5 result in non-uniform and incomplete deactivation, particularly when mixing and mass transfer limitations may prevent contact with all co-catalyst species in an effluent stream, and in circumstances where process conditions such as temperature can vary.

In the relationship between the molar amount of OH of the co-catalyst deactivating agent and the total amount of aluminum reflected by {(moles of aluminum of the aluminoxane)+(moles aluminum of the alkylaluminum)+(moles aluminum of the alkylaluminum)}, the moles of aluminum in the aluminoxane are counted once, whereas the moles of aluminum of the alkylaluminum are counted twice. Again while not wishing to be bound by the following theory, it is believed that approximately one-half to one OH per aluminum is required to deactivate the aluminoxane, whereas approximately two OH groups per aluminum are required to deactivate the alkylaluminum.

The methods and processes disclosed herein can be utilized with any suitable transition metal-based catalyst system that contains a co-catalyst comprising an aluminoxane and optionally an alkylaluminum. The metal in the catalyst system can be chromium, iron, cobalt, vanadium, titanium, zirconium, hafnium, and the like, or any combination thereof. In an aspect, the transition metal-based catalyst system can comprise chromium; alternatively, iron; alternatively, cobalt; alternatively, vanadium; alternatively, titanium; alternatively, zirconium; or alternatively, hafnium.

As above, while not being limited to use with any particular catalyst system, the methods and processes disclosed herein are particularly well suited for use in conjunction with a transition metal-based catalyst system or catalyst system components that comprise (i) a heteroatomic ligand transition metal compound complex and the co-catalyst, or (ii) a heteroatomic ligand, a transition metal compound, and the co-catalyst. Thus, the methods and processes can be used in conjunction with a transition metal-based catalyst system or catalyst system components that comprise (i) a heteroatomic ligand chromium compound complex and the co-catalyst, or (ii) a heteroatomic ligand, a chromium compound, and the co-catalyst. Other catalyst systems for which the disclosed methods and processes are particularly well suited for use include U.S. Pat. Nos. 10,493,422, 10,464,862, 10,435,336, and 11,267,909.

In the methods/processes disclosed herein, the catalyst system is contacted with a $C_4$-$C_{18}$ alcohol co-catalyst deactivating agent. In one aspect, for instance, the co-catalyst deactivating agent can comprise a $C_6$-$C_{16}$ alcohol, while in another aspect, the co-catalyst deactivating agent can comprise a $C_5$-$C_{12}$ alcohol. The term alcohol is used generically to include mono-ols, diols, and polyols, therefore the co-catalyst deactivating agent can comprise a mono alcohol compound, a diol compound, a polyol compound, or any combination thereof.

Consistent with particular aspects of this invention, the co-catalyst deactivating agent can comprise a butanol, a pentanol, a hexanol, a heptanol, an octanol, a nonanol, a decanol, an undecanol, and the like, as well as any mixture or combination thereof. Specific examples of co-catalyst deactivating agents that can be utilized to deactivate the catalyst system include, for instance, 1-butanol, 2-butanol, iso-butanol, sec-butanol, t-butanol, 1-pentanol, cyclopentanol, 1-hexanol, 2-hexanol, 3-hexanol, cyclohexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-nonanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, and the like, as well any mixture or combination thereof. In a particular aspect disclosed herein, the co-catalyst deactivating agent can comprise 2-ethyl-hexanol.

The suitability of a particular co-catalyst deactivating agent with a particular catalyst system can depend upon many factors, one of which is the prevailing temperature when the catalyst system and the co-catalyst deactivating agent are contacted. Thus, a particular boiling point of the co-catalyst deactivating agent may be important. Accordingly, the co-catalyst deactivating agent can have a minimum boiling point (at a pressure of 1 atm) of 130° C., 140° C., 150° C., 160° C., or 170° C.; additionally or alternatively, a maximum boiling point (at a pressure of 1 atm) of 300° C., 280° C., 250° C., or 220° C. Generally, the boiling point of the deactivating agent can be in a range from any minimum temperature disclosed herein to any maximum temperature disclosed herein. Therefore, suitable non-limiting ranges can include the following: from 130° C. to 300° C., from 130° C. to 220° C., from 140° C. to 280° C., from 150° C. to 250° C., from 160° C. to 280° C., from 160° C. to 250° C., from 170° C. to 300° C., or from 170° C. to 220° C. In an oligomerization process, for instance, it can be beneficial for the co-catalyst deactivating agent to stay with the heavier products, such that the co-catalyst deactivating agent is easy to separate from 1-hexene and/or 1-octene, and therefore, a co-catalyst deactivating agent with a boiling point of at least 130° C., and more often, at least 150° C. or at least 170° C. can be advantageous.

Another factor related to the suitability of the co-catalyst deactivating agent is that the deactivated catalyst system components (e.g., alkoxides)—that are formed as a result of contacting the catalyst system with the co-catalyst deactivating agent—beneficially are soluble in the effluent stream (e.g., which contains an organic reaction medium or hydrocarbons) at a minimum temperature of 130° C., 140° C., 150° C., 160° C., or 170° C.; additionally or alternatively, at a maximum temperature of 300° C., 280° C., 250° C., or 220° C. Generally, the deactivated catalyst system components can be soluble in the effluent stream (e.g., containing hydrocarbons) in a range from any minimum temperature disclosed herein to any maximum temperature disclosed herein. Therefore, suitable non-limiting ranges can include the following: from 130° C. to 300° C., from 130° C. to 220° C., from 140° C. to 280° C., from 150° C. to 250° C., from 160° C. to 280° C., from 160° C. to 250° C., from 170° C. to 300° C., or from 170° C. to 220° C. The deactivated catalyst system components are considered soluble if there is no visible precipitation at the respective temperature.

While not required, but generally, contacting the effluent stream or catalyst system with the co-catalyst deactivating agent is a single addition which both deactivates the co-catalyst (e.g., halts oligomerization of ethylene to hexenes and/or octenes, and/or halts isomerization of hexenes and/or octenes) and stops the pyrophoric activity of the co-catalyst (e.g., halts air and moisture reactivity). Thus, beneficially, multiple injections of the same or different deactivating agents with different functions are not required.

Consistent with any of the methods/processes disclosed herein, and optionally, these methods/processes can further include a control system that comprises the steps of (i) determining an amount of catalytic activity remaining after addition of the co-catalyst deactivating agent, and (ii) adjusting the amount of the co-catalyst deactivating agent based on the catalytic activity. For example, if there is some catalytic activity remaining after addition of the co-catalyst deactivating agent, a greater molar amount of OH can be added. Conversely, if there is no catalytic activity, the addition amount may be reduced. The amount of catalytic activity remaining after addition of the co-catalyst deactivating agent can be determined via any suitable method, and one such method is to test the resulting composition for oligomer product isomerization, such as 1-octene isomerization. That is, after addition of the co-catalyst deactivating agent, determine whether the resulting composition can catalyze the isomerization of 1-octene or the isomerization of 1-dodecene, as shown in the examples that follow.

Referring now to the methods/processes in which the effluent stream from an oligomerization reactor is contacted with the co-catalyst deactivating agent, often the effluent stream is contacted with the co-catalyst deactivating agent before the effluent stream is introduced into a separator to remove at least a portion of the unreacted ethylene. In this aspect, the contacting step is after the reactor discharge but before at least a portion of unreacted ethylene is flashed/removed from the effluent stream.

Alternatively, the effluent stream can be contacted with the co-catalyst deactivating agent after at least a portion of the unreacted ethylene has been removed from the effluent stream in a separator. In this aspect, the co-catalyst deactivating agent can be combined with a bottoms stream from a separator/flash vessel after an ethylene removal step.

Among other constituents, the effluent stream contains an oligomer product, which can comprise hexenes and octenes, as well as other $C_4^+$ linear alpha olefins. The amount of octenes in the oligomer product typically can fall within a range from 20 to 99 wt. %, based on the total amount of oligomers in the oligomer product. In an aspect, the minimum amount of octenes in the oligomer product can be 20, 30, or 40 wt. %. In another aspect, the maximum amount of octenes in the oligomer product can be 99, 95, 97.5, 90, 87.5, or 85 wt. %, Generally, the amount of octenes in the oligomer product can range from any minimum amount of octenes in the oligomer product to any maximum amount of octenes in the oligomer product described herein. For instance, the amount of octenes-based on the total weight of oligomers in the oligomer product—can be from 30 to 95 wt. %, from 40 to 95 wt. %, from 40 to 90 wt. %, from 20 to 90 wt. %, from 30 to 87.5 wt. %, from 30 to 85 wt. %, from 40 to 87.5 wt. %, from 40 to 85 wt. %, from 20 to 60 wt. %, from 30 to 55 wt. %, or from 40 to 55 wt. % octenes.

Additionally or alternatively, the oligomer product can contain any suitable amount of hexenes. In an aspect, the minimum amount of hexenes in the oligomer product can be 15, 20, 25, 30, or 35 wt. %. In another aspect, the maximum amount of hexenes in the oligomer product can be 75, 65, 60, 55, or 50 wt. %. Generally, the amount of hexenes in the oligomer product can range from any minimum amount of hexenes in the oligomer product to any maximum amount of hexenes in the oligomer product described herein. For instance, the amount of hexenes—based on the total weight of oligomers in the oligomer product—can be from 20 to 60 wt. %, from 25 to 55 wt. %, or from 30 to 50 wt. % hexenes.

The amount of conversion of ethylene in the oligomerization reactor is not particularly limited, and generally the minimum ethylene conversion can be at least 20, 30, 40, 45, or 50 wt. %, while the maximum ethylene conversion can be 99, 95, 90, 80, 75, or 65 wt. %. Generally, the ethylene conversion in the reactor can range from any minimum conversion to any maximum conversion described herein. For instance, the ethylene conversion can range from 20 to 95 wt. %, from 30 to 90 wt. %, from 40 to 80 wt. %, from 50 to 70 wt. %, or from 55 to 65 wt. %. The ethylene conversion is based on the amount of ethylene entering the reactor and the amount of ethylene in the effluent stream.

Referring now to step A) of the oligomerization process, ethylene, a transition metal-based catalyst system or catalyst system components, an organic reaction medium, and optionally hydrogen, are introduced into an oligomerization reactor, and the transition metal-based catalyst system or catalyst system components contains a co-catalyst comprising an aluminoxane and optionally an alkylaluminum. Hydrogen use is optional in step A), thus in one aspect, hydrogen is not present in step A), while in another aspect, hydrogen is present in step A).

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

GC-FID data was collected on an Agilent Technologies 7890A instrument equipped with a 50 m length Agilent DB-5 GC column with an inner diameter of 0.32 mm and film thickness of 0.25 μm. The sample (0.05 μL) was syringe injected into the inlet with a split ratio of 25:1 at 300° C. using He as the carrier gas. The initial column temperature was ° C. with a temperature ramp rate of 3° C./min up to 80° C., followed by a 13° C./min ramp up to 300° C. and a 15 min hold time. Peak integration was performed manually and peak identification was made using authentic samples.

Examples 1-5

In Examples 1-5, an illustrative chromium/MAO/alkylaluminum catalyst system was used to determine the amount of co-catalyst deactivating agent required to deactivate the co-catalyst components of the catalyst system, and in particular, to prevent the dimerization and/or isomerization of 1-dodecene at 175° C. For Example 1, a vial was charged with 18.2 mg of a representative chromium catalyst (a $N^2$-phosphinyl guanidine chromium(III) trichloride tetrahydrofuran complex), 1 g xylene, and 1 g n-tridecane (internal standard), followed by the co-catalyst. The co-catalyst amounts were 60 equivalents of triethylaluminum (60:1 Al:Cr) and 400 equivalents of MMAO-21 (400:1 Al:Cr). MMAO-21 is a modified methylaluminoxane produced from a mixture of TMA and TIBA. After addition of 10 g of 1-dodecene (~95.2 wt. %), the vial was heated to 175° C. over 30 min and then maintained at that temperature for 1 hr. After cooling to room temperature, the vial contents were fully quenched with water and then analyzed by GC.

Example 2 was a control sample of the 1-dodecene starting material (~95.2 wt. % purity) with no other materials added. Examples 3-5 were performed similarly to Example 1, except that 2-ethyl-1-hexanol co-catalyst deactivating agent was added after the 1-dodecene, but prior to heating to 175° C. The addition amount of 2-ethyl-1-hexanol in Example 3 was a molar amount of OH equal to 1.95 times {(moles of aluminum of the aluminoxane)+(moles aluminum of the alkylaluminum)+(moles aluminum of the alkylaluminum)}. Example 4 was performed with a molar amount of OH equal to 1.60 times {(moles of aluminum of the aluminoxane)+(moles aluminum of the alkylaluminum)+(moles aluminum of the alkylaluminum)}, and Example 5 was performed with a molar amount of OH equal to 1.24 times {(moles of aluminum of the aluminoxane)+(moles aluminum of the alkylaluminum)+(moles aluminum of the alkylaluminum)}. Examples 1-5 are summarized in FIG. 1 and in Table 1 below.

As shown by FIG. 1 and the data in Table 1, Example 1 had significant isomerization and dimerization of the 1-dodecene, as would be expected with no co-catalyst deactivating agent present. However, with the co-catalyst deactivating agent present, Examples 3-5 performed identically to control Example 2 (1-dodecene control). No isomerization or dimerization was found in Examples 3-5, and the 1-dodecene purity was the same as for the 1-dodecene control of Example 2.

It was not surprising that using the 1.95 molar amount in Example 3 would suppress isomerization/dimerization, but it was unexpected that the much lower amount of 1.24 used in Example 5 would perform similarly. This data indicates that much lower amounts of the co-catalyst deactivating agent can be used to successfully deactivate the catalyst system, without introducing excess OH into an oligomerization reactor system with its associated cost and performance drawbacks.

TABLE 1

| Example | Effective amount of quench OH* | 1-dodecene purity (wt. %) | Isomerization | Dimerization |
| --- | --- | --- | --- | --- |
| 1 | 0 | — | ~60% | ~15% |
| 3 | 1.95 | 95.07 | — | — |
| 4 | 1.60 | 95.41 | — | — |
| 5 | 1.24 | 95.14 | — | — |

*The molar amount of OH of the co-catalyst deactivating agent based on {(moles of aluminum of the aluminoxane) + (moles aluminum of the alkylaluminum) + (moles aluminum of the alkylaluminum)}.

Examples 6-10

Examples 6-10 were performed similarly to Examples 1-5, except in Examples 6-10 an illustrative MAO catalyst system was used to determine the amount of co-catalyst deactivating agent required to deactivate the aluminoxane component of the catalyst system (with no alkylaluminum component present in the catalyst system), and in particular, the amount required to prevent the dimerization and/or isomerization of 1-dodecene at 170° C. For Example 6, a vial was charged with 10 g of 7 wt. % MMAO-3A in n-heptane. MMAO-3A is a modified methylaluminoxane produced from a mixture of TMA and TIBA. After addition of 12.5 mL g of 1-dodecene (~95-96 wt. %), the vial was heated to 170° C. over 15 min and then maintained at that temperature for 1 hr. After cooling to room temperature, the vial contents were fully quenched with water and then analyzed by GC.

Example 7 was a control sample of the 1-dodecene starting material (~95-96 wt. % purity) with no other materials added. Examples 8-10 were performed similarly to Example 6, except that 2-ethyl-1-hexanol co-catalyst deactivating agent was added after the 1-dodecene, but prior to heating to 170° C. The addition amount of 2-ethyl-1-hexanol in Example 8 was a molar amount of OH equal to 1.0 times {(moles of aluminum of the aluminoxane)+(moles aluminum of the alkylaluminum)+(moles aluminum of the alkylaluminum)}. Example 9 was performed with a molar amount of OH equal to 0.8 times {(moles of aluminum of the aluminoxane)+(moles aluminum of the alkylaluminum)+(moles aluminum of the alkylaluminum)}. Example 10 was performed with a molar amount of OH equal to 0.6 times {(moles of aluminum of the aluminoxane)+(moles aluminum of the alkylaluminum)+(moles aluminum of the alkylaluminum)}. Note that no alkylaluminum co-catalyst was present in the catalyst systems of Examples 6-10. Examples 6-10 are summarized in Table 2 below.

As shown in Table 2, Example 6 had significant isomerization and dimerization of the 1-dodecene, as would be expected with no co-catalyst deactivating agent present. However, with the co-catalyst deactivating agent present, Examples 8-10 performed identically to control Example 7 (1-dodecene control). No isomerization or dimerization was found in Examples 8-10. The GC data for Examples 6-10 was also confirmed using NMR, which demonstrated that Examples 7-10 each contained the same amount of alpha olefin and internal olefin (no isomerization).

It was surprising that using the 1.0 and the 0.8 molar amounts, respectively, in Example 8 and Example 9 would completely suppress isomerization/dimerization. However, it was even more unexpected that using the effective amount of quench OH equal to 0.6 in Example 10 would also perform similarly. This data indicates that much lower amounts of the co-catalyst deactivating agent can be used to successfully deactivate the catalyst system, without introducing excess OH into an oligomerization reactor system with its associated cost and performance drawbacks.

TABLE 2

| Example | Effective amount of quench OH* | Comments |
| --- | --- | --- |
| 6 | 0 | 65 wt. % 1-dodecene remained, the balance was isomerized or dimerized |
| 8 | 1.0 | No isomerization or dimerization |
| 9 | 0.8 | No isomerization or dimerization |
| 10 | 0.6 | No isomerization or dimerization |

*The molar amount of OH of the co-catalyst deactivating agent based on {(moles of aluminum of the aluminoxane) + (moles aluminum of the alkylaluminum) + (moles aluminum of the alkylaluminum)}.

The invention is described herein with reference to numerous aspects and specific examples. Many variations will suggest themselves to those skilled in the art in light of the detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A method for deactivating a transition metal-based catalyst system (e.g., a residual catalyst system) containing a co-catalyst comprising an aluminoxane and optionally an alkylaluminum, the method comprising:

contacting the catalyst system with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

Aspect 2. A method for deactivating a residual transition metal-based catalyst system containing a co-catalyst comprising an aluminoxane and optionally an alkylaluminum in an effluent stream from an oligomerization reactor, the method comprising:

contacting the effluent stream, the effluent stream comprising unreacted ethylene, an oligomer product, the residual transition metal-based catalyst system containing the co-catalyst comprising the aluminoxane and optionally the alkylaluminum, and an organic reaction medium, with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+ (moles aluminum of the alkylaluminum)}.

Aspect 3. An oligomerization process comprising:
A) introducing ethylene, a transition metal-based catalyst system or catalyst system components, an organic reaction medium, and optionally hydrogen, into an oligomerization reactor, the transition metal-based catalyst system or catalyst system components containing a co-catalyst comprising a aluminoxane and optionally an alkylaluminum;
B) forming an oligomer product in the oligomerization reactor, the oligomer product comprising hexenes and octenes;
C) discharging an effluent stream from the oligomerization reactor, the effluent stream comprising unreacted ethylene, the oligomer product, a residual transition metal-based catalyst system containing the co-catalyst comprising the aluminoxane and optionally the alkylaluminum, and the organic reaction medium; and
D) contacting the effluent stream with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+ (moles aluminum of the alkylaluminum)+(moles aluminum of the alkylaluminum)}.

Aspect 4. The method or process defined in aspect 2 or 3, wherein the effluent stream is contacted with the co-catalyst deactivating agent before the effluent stream is introduced into a separator to remove at least a portion of the unreacted ethylene.

Aspect 5. The method or process defined in aspect 2 or 3, wherein the effluent stream is contacted with the co-catalyst deactivating agent after at least a portion of the unreacted ethylene has been removed from the effluent stream in a separator.

Aspect 6. The method or process defined in any one of the preceding aspects, wherein the alkylaluminum comprises trimethylaluminum (TMA), triethylaluminum (TEA), tri-n-propylaluminum (TNPA), tri-n-butylaluminum (TNBA), tri-isobutylaluminum (TIBA), tri-n-hexylaluminum, tri-n-octylaluminum, or any combination thereof.

Aspect 7. The method or process defined in any one of the preceding aspects, wherein the aluminoxane comprises methylaluminoxane (MAO), modified methylaluminoxane (MMAO), ethylaluminoxane, n-propylaluminoxane, iso-propyl-aluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, or any combination thereof.

Aspect 8. The method or process defined in any one of the preceding aspects, wherein a molar ratio of aluminoxane: alkylaluminum based on aluminum is in any range disclosed herein, e.g., from 100:1 to 1:100, from 20:1 to 1:20, from 10:1 to 1:10, from 5:1 to 1:5, from 10:1 to 1:1, or from 8:1 to 2:1.

Aspect 9. The method or process defined in any one of the preceding aspects, wherein the transition metal-based catalyst system comprises chromium, iron, cobalt, vanadium, titanium, zirconium, hafnium, or a combination thereof.

Aspect 10. The method or process defined in any one of the preceding aspects, wherein the co-catalyst deactivating agent comprises a mono alcohol compound, a diol compound, a polyol compound (or alternatively, a mono alcohol compound), and the co-catalyst deactivating agent comprises a $C_4$-$C_{18}$ alcohol, a $C_6$-$C_{16}$ alcohol, or a $C_8$-$C_{12}$ alcohol.

Aspect 11. The method or process defined in any one of the preceding aspects, wherein the co-catalyst deactivating agent comprises a butanol, a pentanol, a hexanol, a heptanol, an octanol, a nonanol, a decanol, an undecanol, or mixtures thereof.

Aspect 12. The method or process defined in any one of the preceding aspects, wherein the co-catalyst deactivating agent comprises 1-butanol, 2-butanol, iso-butanol, sec-butanol, t-butanol, 1-pentanol, cyclopentanol, 1-hexanol, 2-hexanol, 3-hexanol, cyclohexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-nonanol, 1-decanol, 2-decanol, 3-decanol, 4-decanol, 5-decanol, 1-undecanol, 2-undecanol, 7-methyl-2-decanol, a 1-dodecanol, a 2-dodecanol, 2-ethyl-1-decanol, or mixtures thereof.

Aspect 13. The method or process defined in any one of the preceding aspects, wherein the co-catalyst deactivating agent comprises 2-ethyl-hexanol.

Aspect 14. The method or process defined in any one of the preceding aspects, wherein the co-catalyst deactivating agent has a boiling point (at a pressure of 1 atm) in any range disclosed herein, e.g., at least 130° C., at least 140° C., at least 150° C., at least 160° C., or at least 170° C., and less than or equal to 300° C., less than or equal to 280° C., less than or equal to 250° C., or less than or equal to 220° C.

Aspect 15. The method or process defined in any one of aspects 2-14, wherein contacting with the co-catalyst deactivating agent forms deactivated catalyst system components (e.g., alkoxides), and the deactivated catalyst system components are soluble in the effluent stream (e.g., organic reaction medium, hydrocarbons) at any temperature disclosed herein, e.g., at least 130° C., at least 140° C., at least 150° C., at least 160° C., or at least 170° C., and less than or equal to 300° C., less than or equal to 280° C., less than or equal to 250° C., or less than or equal to 220° C.

Aspect 16. The method or process defined in any one of the preceding aspects, wherein contacting with the co-catalyst deactivating agent is a single addition which both deactivates the co-catalyst (e.g., halts oligomerization of ethylene to hexenes and/or octenes or isomerization of hexenes and/or octenes) and stops pyrophoric activity of the co-catalyst (e.g., halts air and moisture reactivity).

Aspect 17. The method or process defined in any one of the preceding aspects, wherein the method or process is performed continuously.

Aspect 18. The method or process defined in any one of the preceding aspects, wherein the transition metal-based catalyst system or catalyst system components comprise (i) a heteroatomic ligand transition metal compound complex and the co-catalyst, or (ii) a heteroatomic ligand, a transition metal compound, and the co-catalyst.

Aspect 19. The method or process defined in any one of the preceding aspects, wherein the transition metal-based catalyst system or catalyst system components comprise (i) a heteroatomic ligand chromium compound complex and the co-catalyst, or (ii) a heteroatomic ligand, a chromium compound, and the co-catalyst.

Aspect 20. The method or process defined in any one of aspects 2-19, wherein the oligomer product comprises any amount of octenes disclosed herein, e.g., at least 20, 30 or 40 wt. %; a maximum of 99, 95, 92.5, 90, 87.5, or 85 wt. %; or from 20 to 99 wt. %, from to 95 wt. %, from 40 to 95 wt. %, from 40 to 90 wt. %, from 20 to 90 wt. %, from 30 to 87.5 wt. %, from 30 to 85 wt. %, from 40 to 87.5 wt. %, from 40 to 85 wt. %, from 20 to 60 wt. %, from 30 to 55 wt. %, or from 40 to 55 wt. % octenes, based on the total amount of oligomers in the oligomer product.

Aspect 21. The method or process defined in any one of aspects 2-20, wherein the oligomer product comprises any amount of hexenes disclosed herein, e.g., at least 15, 20, 30, or 35 wt. %; a maximum of 75, 65, 60, 55, or 50 wt. %; or from 20 to 60 wt. %, from to 55 wt. %, or from 30 to 50 wt. % hexenes, based on the total amount of oligomers in the oligomer product.

Aspect 22. The process defined in any one of aspects 3-21, wherein the oligomerization reactor has any ethylene conversion disclosed herein, e.g., at least 20, 30, 35, 45, or 50 wt. %; a maximum of 99, 95, 90, 80, 75, 70, or 65 wt. %; or from 20 to 95 wt. %, from 30 to 90 wt. %, from 40 to 80 wt. %, from 50 to 70 wt. %, or from 55 to 65 wt. % conversion, based on the amount of ethylene entering the reactor and the amount of ethylene in the effluent stream.

Aspect 23. The process defined in any one of aspects 3-22, wherein hydrogen is present in step A).

Aspect 24. The method or process defined in any one of the preceding aspects, further comprising the steps of:
(i) determining an amount of catalytic activity remaining after addition of the co-catalyst deactivating agent (e.g., test the product for oligomer product isomerization, such as 1-octene isomerization); and
(ii) adjusting the amount of the co-catalyst deactivating agent based on the catalytic activity.

Aspect 25. The method or process defined in any one of the preceding aspects, wherein the molar amount of OH is in any range disclosed herein, e.g., at least 0.6, at least at least 0.8, at least 0.9, at least 1, or at least 1.1, and less than or equal to 1.5, less than or equal to 1.4, less than or equal to 1.3, or less than or equal to 1.2, times {(moles of aluminum of the aluminoxane)+(moles aluminum of the alkylaluminum)+(moles aluminum of the alkylaluminum)}.

Aspect 26. The method or process defined in any one of the preceding aspects, wherein the co-catalyst comprises the aluminoxane and the alkylaluminum (or alternatively, the aluminoxane and no alkylaluminum).

What is claimed is:

1. An oligomerization process comprising:
A) introducing ethylene, a transition metal-based catalyst system or catalyst system components, an organic reaction medium, and optionally hydrogen, into an oligomerization reactor, the transition metal-based catalyst system or catalyst system components containing a co-catalyst comprising an aluminoxane and optionally an alkylaluminum;
B) forming an oligomer product in the oligomerization reactor, the oligomer product comprising hexenes and octenes;
C) discharging an effluent stream from the oligomerization reactor, the effluent stream comprising unreacted ethylene, the oligomer product, a residual transition metal-based catalyst system containing the co-catalyst comprising the aluminoxane and optionally the alkylaluminum, and the organic reaction medium; and
D) contacting the effluent stream with a $C_4$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

2. The process of claim 1, wherein the effluent stream is contacted with the co-catalyst deactivating agent before the effluent stream is introduced into a separator to remove at least a portion of the unreacted ethylene.

3. The process of claim 1, wherein the effluent stream is contacted with the co-catalyst deactivating agent after at least a portion of the unreacted ethylene has been removed from the effluent stream in a separator.

4. The process of claim 1, wherein:
the co-catalyst comprises the alkylaluminum;
the alkylaluminum comprises trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, or any combination thereof; and
the aluminoxane comprises methylaluminoxane (MAO), modified methylaluminoxane (MMAO), ethylaluminoxane, n-propylaluminoxane, iso-propylaluminoxane, n-butylaluminoxane, t-butylaluminoxane, sec-butylaluminoxane, iso-butylaluminoxane, 1-pentyl-aluminoxane, 2-pentylaluminoxane, 3-pentylaluminoxane, isopentylaluminoxane, neopentylaluminoxane, or any combination thereof.

5. The process of claim 1, wherein the co-catalyst deactivating agent has a boiling point at a pressure of 1 atm of at least 150° C.

6. The process of claim 1, wherein the co-catalyst deactivating agent comprises 2-ethyl-1-hexanol.

7. The process of claim 1, wherein the transition metal-based catalyst system or catalyst system components comprise (i) a heteroatomic ligand chromium compound complex and the co-catalyst, or (ii) a heteroatomic ligand, a chromium compound, and the co-catalyst.

8. The process of claim 1, wherein the oligomer product comprises from 30 to 87.5 wt. % octenes, based on the total amount of oligomers in the oligomer product.

9. The process of claim 1, wherein the oligomer product comprises from 20 to 60 wt. % hexenes, based on the total amount of oligomers in the oligomer product.

10. The process of claim 1, wherein hydrogen is present in step A).

11. The process of claim 1, further comprising the steps of:
(i) determining an amount of catalytic activity remaining after addition of the co-catalyst deactivating agent; and
(ii) adjusting the amount of the co-catalyst deactivating agent based on the catalytic activity.

12. The process of claim 1, wherein the molar amount of OH is from 0.6 to 1.4 times {(moles of aluminum of the aluminoxane)+(moles aluminum of the alkylaluminum)+(moles aluminum of the alkylaluminum)}.

13. The process of claim 1, wherein the co-catalyst does not contain the alkylaluminum.

14. The process of claim 1, wherein a molar ratio of aluminoxane:alkylaluminum based on aluminum is from 10:1 to 1:10.

15. A method for deactivating a residual transition metal-based catalyst system containing a co-catalyst comprising an aluminoxane and optionally an alkylaluminum in an effluent stream from an oligomerization reactor, the method comprising:
contacting the effluent stream, the effluent stream comprising unreacted ethylene, an oligomer product, the residual transition metal-based catalyst system containing the co-catalyst comprising the aluminoxane and optionally the alkylaluminum, and an organic reaction medium, with a $C_{14}$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

16. The method of claim 15, wherein the molar amount of OH is from 0.6 to 1.3 times {(moles of aluminum of the aluminoxane)+(moles aluminum of the alkylaluminum)+(moles aluminum of the alkylaluminum)}.

17. The method of claim 15, wherein the catalyst system comprises chromium, iron, cobalt, vanadium, titanium, zirconium, hafnium, or a combination thereof.

18. A method for deactivating a transition metal-based catalyst system containing a co-catalyst comprising an aluminoxane and optionally an alkylaluminum, the method comprising:
    contacting the catalyst system with a $C_{14}$-$C_{18}$ alcohol co-catalyst deactivating agent at a molar amount of OH of the co-catalyst deactivating agent in a range from 0.5 to 1.5 times {(moles of aluminum of the aluminoxane)+(moles aluminum of the alkylaluminum)+(moles aluminum of the alkylaluminum)}.

19. The method of claim 18, wherein the molar amount of OH is from 0.6 to 1.5 times {(moles of aluminum of the aluminoxane)+(moles aluminum of the alkylaluminum)+(moles aluminum of the alkylaluminum)}.

20. The method of claim 18, wherein:
    the co-catalyst comprises the alkylaluminum; and
    the co-catalyst deactivating agent comprises a butanol, a pentanol, a hexanol, a heptanol, an octanol, a nonanol, a decanol, an undecanol, or mixtures thereof.

21. The process of claim 2, wherein the co-catalyst deactivating agent comprises 2-ethyl-1-hexanol.

22. The process of claim 21, further comprising the steps of:
    (i) determining an amount of catalytic activity remaining after addition of the co-catalyst deactivating agent; and
    (ii) adjusting the amount of the co-catalyst deactivating agent based on the catalytic activity.

23. The process of claim 21, wherein a molar ratio of aluminoxane:alkylaluminum based on aluminum is from 10:1 to 1:10.

24. The process of claim 3, wherein the co-catalyst deactivating agent comprises 2-ethyl-1-hexanol.

* * * * *